United States Patent
Pivovarov

(10) Patent No.: US 6,675,804 B1
(45) Date of Patent: Jan. 13, 2004

(54) SNORE AND TEETH GRINDING PREVENTION AND TREATMENT

(76) Inventor: Alexander R. Pivovarov, 10189 W. Sample Rd., Coral Springs, FL (US) 33065

( * ) Notice: Subject to any disclaimer, the term of this patent is extended or adjusted under 35 U.S.C. 154(b) by 0 days.

(21) Appl. No.: 10/424,680

(22) Filed: Apr. 28, 2003

(51) Int. Cl.[7] ................................. A61F 5/56
(52) U.S. Cl. .................. 128/848; 128/859; 128/860; 128/861; 128/862; 602/902
(58) Field of Search .................. 128/848, 859–862; 602/902; 433/6

(56) References Cited

U.S. PATENT DOCUMENTS

| | | | | |
|---|---|---|---|---|
| 3,139,088 A | * | 6/1964 | Gulleher ................ | 128/848 |
| 3,692,025 A | * | 9/1972 | Greenberg | |
| 4,270,531 A | * | 6/1981 | Blachly ................ | 128/207.14 |
| 5,253,658 A | * | 10/1993 | King ................... | 128/859 |
| 5,533,523 A | * | 7/1996 | Bass ................... | 128/861 |
| 5,921,240 A | | 7/1999 | Gall | |
| 2002/0144685 A1 | * | 10/2002 | Ivanovich ............ | 128/848 |

* cited by examiner

Primary Examiner—Michael A. Brown
(74) Attorney, Agent, or Firm—Mark D. Bowen, Esq.; Stearns Weaver Miller Weissler Alhadeff & Sitterson, P.A.

(57) ABSTRACT

An apparatus adapted for partial insertion within the user's mouth for preventing snoring, teeth grinding, and light forms of sleep apnea is disclosed. The apparatus includes a multi-lobed tongue receiving structure, an undulating connector for connecting the multi-lobed structure to an inner lip plate, a hollow tube connecting the lip plate to a dome-shaped structure formed on an outer shield. The device is inserted within the oral cavity of the user in an operative configuration such that movement of the tongue is restrained within the multi-lobed structure, and the teeth clamp down upon the undulating connector with the lip plate positioned between the teeth and the inner portions of the upper and lower lips. As a result of proper application of the apparatus breathing at night is normalized, while snoring, grinding of the teeth, and apnea are prevented.

8 Claims, 7 Drawing Sheets

SNORE AND TEETH GRINDING PREVENTION AND TREATMENT

CROSS REFERENCE TO RELATED APPLICATIONS

N/A

STATEMENT REGARDING FEDERALLY SPONSORED RESEARCH OR DEVELOPMENT

N/A

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark Office patent file or records, but otherwise reserves all copyrights.

BACKGROUND OF THE INVENTION

1. Field of the Invention

The present invention relates to devices for preventing snoring, teeth grinding, and light forms of sleep apnea, and more particularly, to mouth piece for personal use for the treatment and prevention of uncomplicated snoring, light forms of obstructive apnea syndrome, and grinding of the teeth during sleep.

2. Description of the Background Art

Snoring is caused by vibration of the uvula or the soft palate in the interior of the mouth when a person breathes through his/her mouth while sleeping. The act of snoring results in an irritating sound capable of disturbing sleep patterns of many, including the person snoring. In addition to the irritating snoring sound, many consider mouth breathing to be unhealthy as it contributes to dry mouth syndrome, as well as contributing to the development of gum disease.

In addition, many people are afflicted with sleep apnea. There are three types of apnea: obstructive, central, and mixed; of the three, obstructive is the most common. Despite the difference in the root cause of each type, in all three, people with untreated sleep apnea stop breathing repeatedly during their sleep, sometimes hundreds of times during the night and often for a minute or longer. Obstructive sleep apnea (OSA) is caused by a blockage of the airway, usually when the soft tissue in the rear of the throat collapses and closes during sleep. With each apnea event, the brain briefly arouses people with sleep apnea in order for them to resume breathing, but consequently sleep is extremely fragmented and of poor quality.

Sleep apnea is very common, as common as adult diabetes, and affects more than twelve million Americans, according to the National Institutes of Health. Risk factors include being male, overweight, and over the age of forty, but sleep apnea can strike anyone at any age, even children. Yet still because of the lack of awareness by the public and healthcare professionals, the vast majority remain undiagnosed and therefore untreated, despite the fact that this serious disorder can have significant consequences.

A further abnormality experienced by many during sleep relates to gritting or grinding of one's teeth, particularly during times of stress. This disorder, refereed to as bruxism, affects numerous people at one time or another. Constant gritting of the teeth can, over time, result in the wearing away of the enamel and misshapen teeth. In severe cases, grinding of the teeth can result in loose or fractured teeth.

As a result there exists a need for a mouthpiece apparatus designed for the prevention and treatment of snoring, light forms of sleep apnea, and gritting of the teeth.

BRIEF SUMMARY OF THE INVENTION

The present invention provides an apparatus adapted for partial insertion within the mouth of a user for preventing snoring, teeth grinding, and light forms of sleep apnea. The apparatus includes a semi-spherical multi-lobed structure for positioning and/or restraining movement of the tongue, an undulating connector for connecting the multi-lobed structure to a flanged lip plate structure adapted to be received between the user's lips and teeth, and a hollow tube connecting the lip plate to a dome-shaped structure formed on an outer shield. The device is positioned within the oral cavity of the user in an operative configuration such that the tongue is retained within the multi-lobed structure, the teeth clamp down upon the undulating connector with the lip plate positioned between the teeth and the inner portions of the upper and lower lips. As a result of proper application of the apparatus breathing at night is normalized, while snoring, grinding of the teeth, and apena are prevented.

Accordingly, it is an object of the present invention to provide an apparatus for preventing snoring and grinding of the teeth during sleep.

Yet another object of the present invention is to provide an apparatus that prevents snoring while enabling the user to breathe through the mouth.

In accordance with these and other objects, which will become apparent hereinafter, the instant invention will now be described with particular reference to the accompanying drawings.

BRIEF DESCRIPTION OF THE SEVERAL VIEWS OF THE DRAWINGS

The drawings furnished herewith illustrate a preferred construction of the present invention in which the above advantages and features are clearly disclosed as well as other which will be readily understood from the following description of the illustrated embodiment.

DETAILED DESCRIPTION OF THE INVENTION

Figure 1:
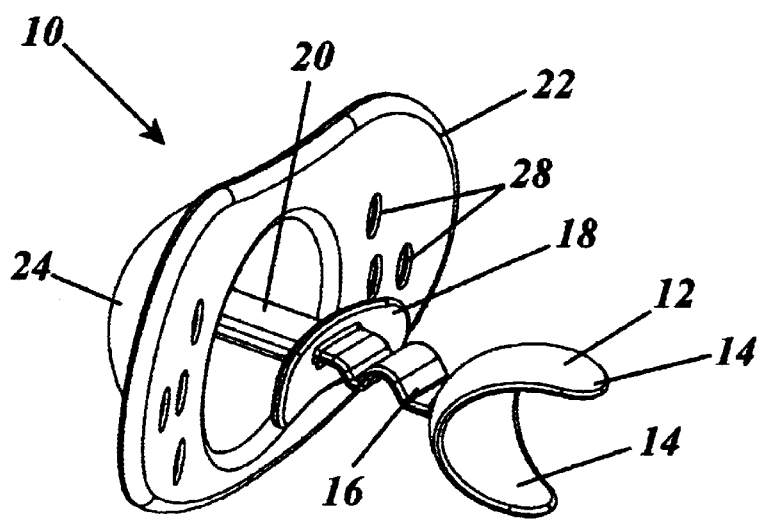
FIG. 1 is a bottom rear perspective view of an apparatus according to the present invention.
Figure 2:
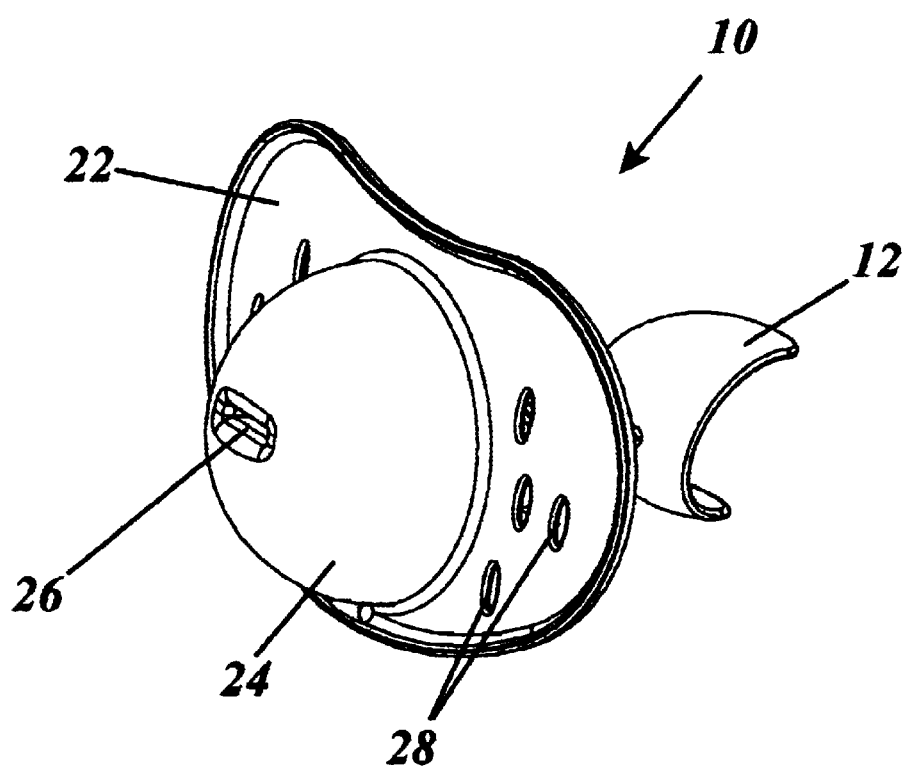
FIG. 2 is a front perspective view thereof.
Figure 3:
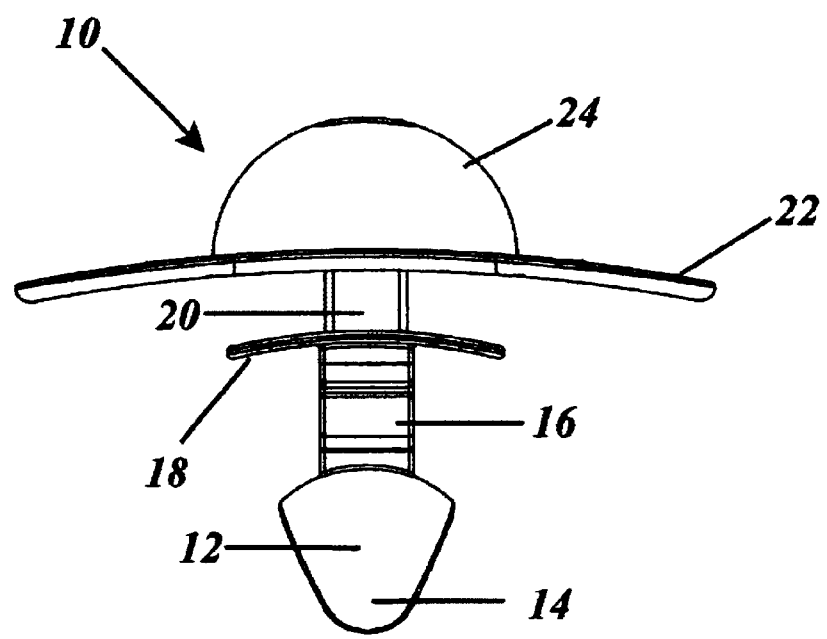
FIG. 3 is a top view thereof.
Figure 4:
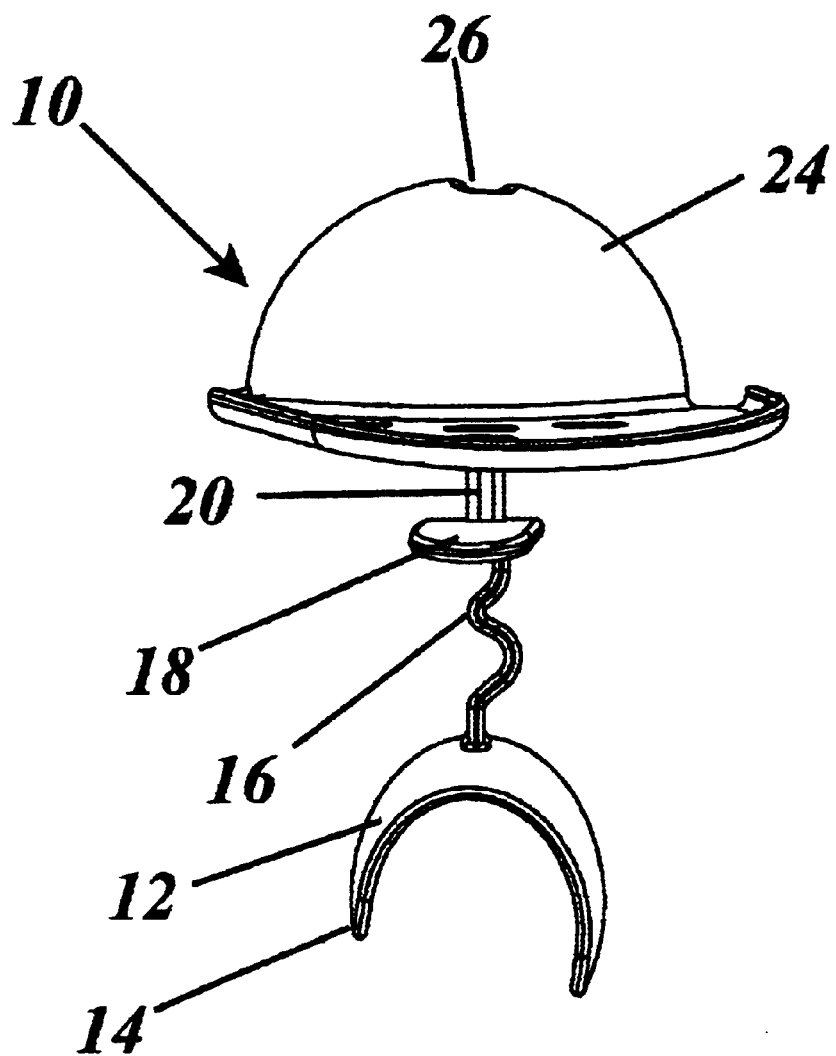
FIG. 4 is a side perspective view thereof.
Figure 5:
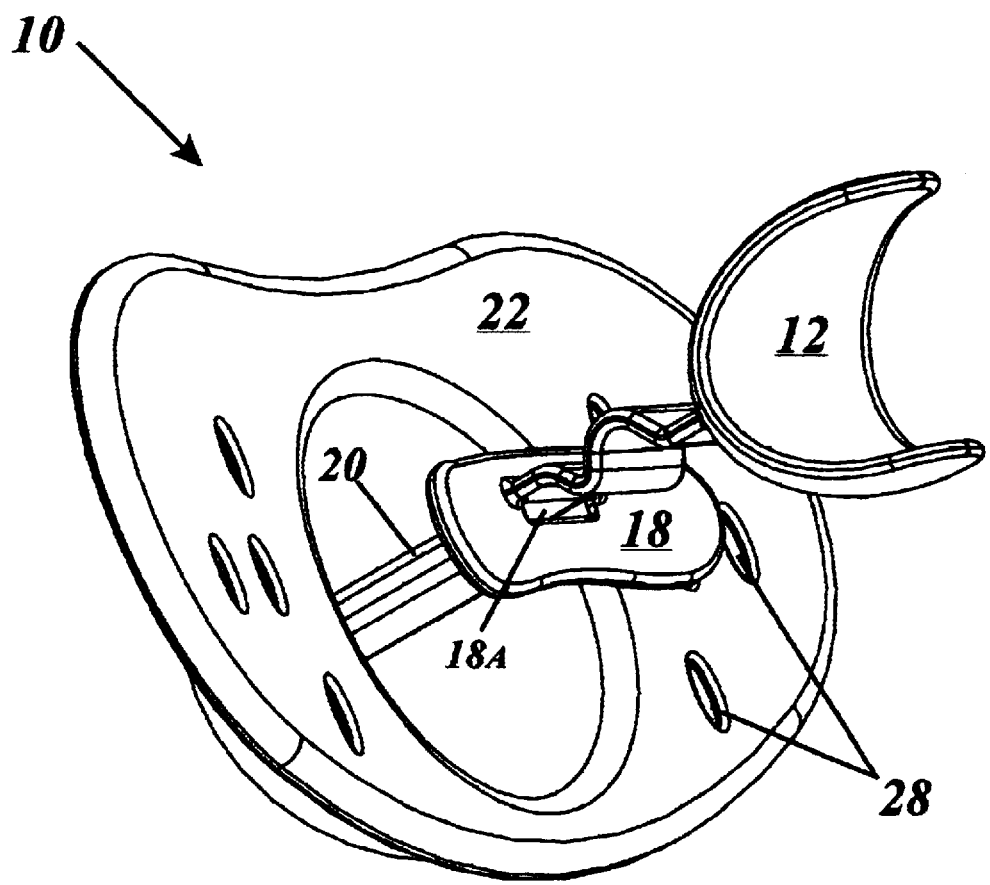
FIG. 5 is a top rear perspective view thereof.
Figure 6:
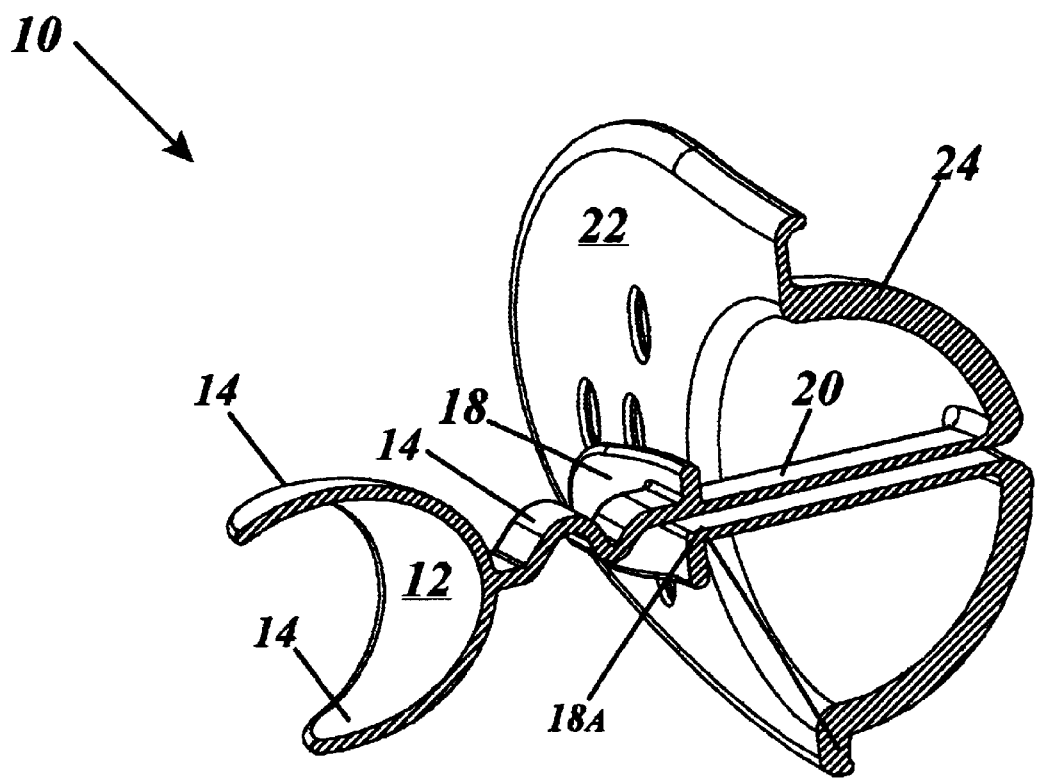
FIG. 6 is a side cross-sectional view thereof.

Referring to FIGS. 1–7, the snore prevention apparatus of the present invention is generally designated by the reference numeral 10. Snore prevention apparatus 10 is designed for preventing snoring, teeth grinding, and/or light forms of obstructive apnea when worn by a user during periods of sleep. As more fully discussed herein, snore prevention apparatus 10 is configured as a mouthpiece, sized and shaped for so as to remain comfortably inserted within the oral cavity of the user during sleep.

As discussed above, snore prevention apparatus 10 is designed for positioning within the mouth of a user. The mouth includes a cavity that terminates externally at upper and lower lips, and internally at the pharynx or gullet. The mouth encloses an upper mandible having upper gums and teeth depending therefrom, and a lower mandible likewise terminating at a lower gum with lower teeth extending upwardly therefrom.

Apparatus 10 includes a tongue receiving structure 12 shaped as a semi-spherically curved oval defining vertically disposed upper and lower lobes, referenced as 14, for positioning and/or restraining the tongue when in use. Tongue retaining structure 12 is attached to an undulating flexible connector 16 having a first end projecting from the convex side thereof and a second end attached to a flanged lip plate 18. More particularly, connector 16 is formed of resilient material shaped in an undulating sine wave pattern that allows for some degree of freedom of movement for the tongue retaining structure 12 for comfort and adjustability. Lip plate 18 is a generally oval flanged structure designed to fit comfortably between the user's upper and lower front teeth and lips. Lip plate 18 defines an aperture 18A in communication with an air tube 20 which functions to define an air flow conduit from the interior of the oral cavity to the atmosphere for allowing the user to breathe while using the apparatus. Air tube 20 is connected to an outer shield component 22, and more particularly to a dome-shaped structure 24 defining an air inlet aperture 26. The outer shield further defines a plurality of ventilation apertures 28 for ventilating the area surrounding the user's mouth when apparatus 10 is in use. The snore prevention apparatus 10 is preferably molded from a pliable, plastic material, such as medical grade silicon material certified for direct contact with mucous and blood.

Figure 7:
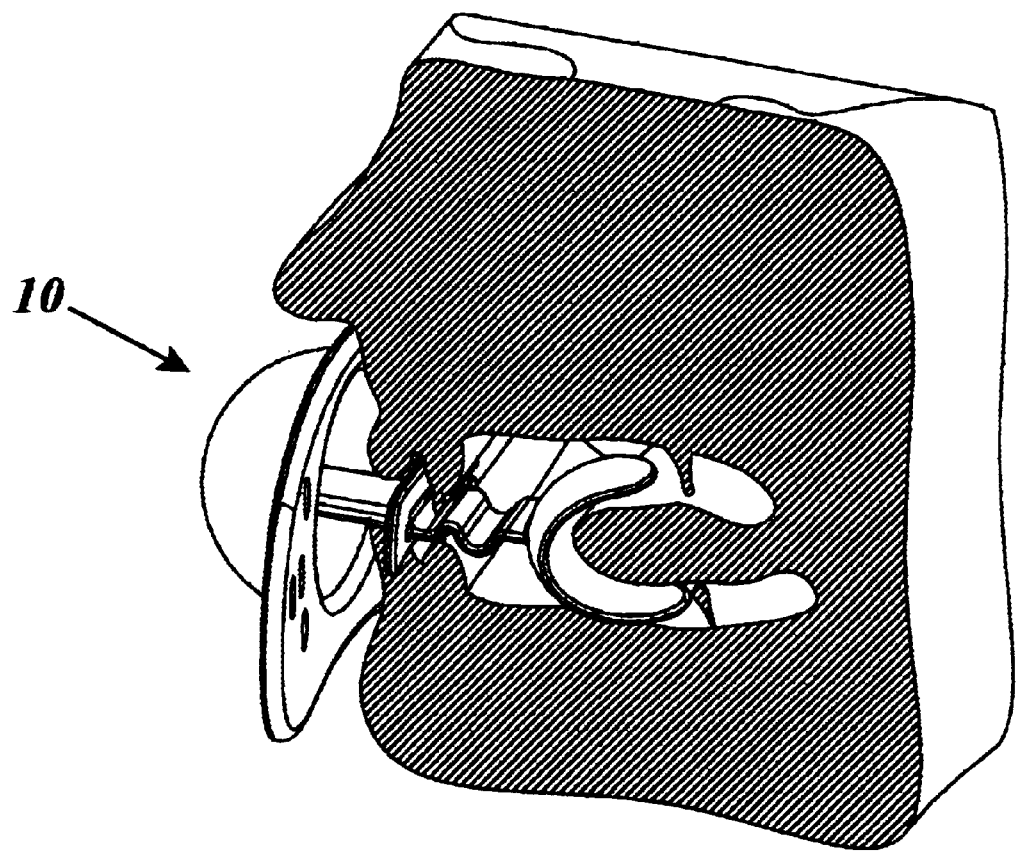
FIG. 7 is a side perspective view illustrating position of the device in use.

In operation, the user inserts the snore prevention apparatus within the oral cavity in an operative configuration such that the tongue is received within the retaining structure 12, the teeth clamp down upon the undulating connector 16 with the flanged lip plate positioned between the upper and lower teeth and the inner portions of the upper and lower lips as best depicted in FIG. 7. As a result of proper application of the apparatus breathing at night is normalized, while snoring, grinding of the teeth, and light sleep apena, are prevented.

The user may become accustomed to the device by wearing it for a few minutes before going to bed for a period of time. Once the user feels comfortable with the device, it may be worn in the mouth all night while sleeping. Should the device become dislodged from the oral cavity during the night, the user may secure the device within the oral cavity using surgical tape. The duration of treatment depends on the severity of the abnormality and the condition of the tissues lining the oral cavity. It has been found, however, that use of the device for a period of some 15–20 days has proven successful in substantially reducing and/or eliminating snoring, whereafter use of the device may be terminated. In the case of recurring snoring, use of the device may recommence for a period of several nights.

The instant invention has been shown and described herein in what is considered to be the most practical and preferred embodiment. It is recognized, however, that departures may be made therefrom within the scope of the invention and that obvious structural and/or functional modifications will occur to a person skilled in the art.

What is claimed is:

1. An apparatus for placement within the mouth of a user, the mouth having an exterior portion terminating in upper and lower lips, a posterior portion, and upper and lower gums therebetween, each gum having teeth projecting therefrom, said apparatus comprising:

an outer plate including a projecting dome, said dome defining an aperture;

an elongate air tube having a first end thereof connected to said dome in fluid communication with said dome aperture;

an inner plate attached to an opposing second end of said air tube, said inner plate sized for insertion in the mouth between the teeth and the lips, said inner plate defining an aperture in fluid communication with said air tube second end;

an elongate tab having a first end connected to said inner plate and a second end connected to a tongue retaining structure; and means for receiving a portion of the user's tongue.

2. An apparatus for placement within the mouth of a user according to claim 1, wherein said elongate tab is flexible.

3. An apparatus for placement within the mouth of a user according to claim 1, wherein said elongate tab is undulating.

4. An apparatus for placement within the mouth of a user according to claim 1, wherein said elongate tab is connected to said inner plate below said inner plate aperture.

5. An apparatus for placement within the mouth of a user according to claim 1, wherein said means for receiving a portion of the user's tongue includes a concave structure.

6. An apparatus for placement within the mouth of a user, the mouth having an exterior portion terminating in upper and lower lips, a posterior portion, and upper and lower gums therebetween, each gum having teeth projecting therefrom, said apparatus comprising:

an outer plate defining a projecting dome, said dome defining an aperture;

an elongate air tube connected to said dome in fluid communication with said dome aperture;

an inner plate attached to an opposing end of said air tube, said inner plate sized for receipt in the mouth between the teeth and the lips, said inner plate defining an aperture in fluid communication with air tube;

an elongate flexible tab having a first end connected to said inner plate and a second end connected to a tongue retaining structure, said elongate tab including an undulating mid-portion;

said tongue retaining structure defining a concave surface terminating in upper and lower projecting lobes.

7. An apparatus for placement within the mouth of a user according to claim 6, wherein said outer plate further defines a plurality of apertures for providing ventilation.

8. An apparatus for placement within the mouth of a user according to claim 6, wherein said apparatus is fabricated from a medical grade polymer.

\* \* \* \* \*